(12) United States Patent
Hagler

(10) Patent No.: US 7,262,846 B2
(45) Date of Patent: Aug. 28, 2007

(54) ENCODER SPECTROGRAPH FOR ANALYZING RADIATION USING SPATIAL MODULATION OF RADIATION DISPERSED BY WAVELENGTH

(75) Inventor: Thomas W. Hagler, Grass Valley, CA (US)

(73) Assignee: Aspectrics, Inc., Pleasanton, CA (US)

( * ) Notice: Subject to any disclaimer, the term of this patent is extended or adjusted under 35 U.S.C. 154(b) by 0 days.

(21) Appl. No.: 11/169,824

(22) Filed: Jun. 28, 2005

(65) Prior Publication Data

US 2005/0286049 A1 Dec. 29, 2005

Related U.S. Application Data

(60) Provisional application No. 60/583,834, filed on Jun. 28, 2004, provisional application No. 60/637,148, filed on Dec. 16, 2004.

(51) Int. Cl.
*G01J 3/28* (2006.01)
*G01J 3/18* (2006.01)

(52) U.S. Cl. .................. 356/330; 356/305; 356/310; 356/328

(58) Field of Classification Search ................ 356/305, 356/310, 326, 328, 330, 332, 334
See application file for complete search history.

(56) References Cited

U.S. PATENT DOCUMENTS

| | | | |
|---|---|---|---|
| 2,631,489 A | 3/1953 | Golay | |
| 3,563,654 A | 2/1971 | Vermande | |
| 3,578,980 A | 5/1971 | Decker | |
| 3,586,442 A | 6/1971 | Tripp | |
| 3,639,062 A | 2/1972 | Girard | |
| 3,640,625 A | 2/1972 | Ibbett | |
| 3,720,469 A | 3/1973 | Harwit | |
| 3,811,777 A | 5/1974 | Chance | |
| 3,922,092 A | 11/1975 | van den Bosch | |
| 4,007,989 A | 2/1977 | Wajda | |
| 4,264,205 A | 4/1981 | Landa | |
| 4,304,491 A | 12/1981 | Kraushaar et al. | |
| 4,448,529 A | 5/1984 | Krause | |
| 4,450,459 A | 5/1984 | Turner et al. | |
| 5,024,508 A | 6/1991 | Horner | |

(Continued)

FOREIGN PATENT DOCUMENTS

GB    672758 A    5/1952

(Continued)

OTHER PUBLICATIONS

Golay, M., "Static Multislit Spectroscopy and Its Application to the Panoramic Display of Infrared Spectra," Journal of the Optical Society of America, Jul. 1951, pp. 468-472, vol. 41, No. 7..

(Continued)

*Primary Examiner*—F. L. Evans
(74) *Attorney, Agent, or Firm*—Fenwick & West LLP

(57) ABSTRACT

An encoder spectrograph is used to analyze radiation from one or more samples in various configurations. The radiation is analyzed by spatially modulating the radiation after it has been dispersed by wavelength or imaged along a line. Dual encoder spectrographs may be used to encode radiation using a single modulator.

30 Claims, 6 Drawing Sheets

U.S. PATENT DOCUMENTS

| | | | |
|---|---|---|---|
| 5,090,807 A | 2/1992 | Tai | |
| 5,121,239 A | 6/1992 | Post | |
| 5,235,461 A | 8/1993 | Kirsch et al. | |
| 5,325,324 A | 6/1994 | Rentzepis et al. | |
| 5,483,335 A | 1/1996 | Tobias | |
| 5,485,268 A | 1/1996 | Tobias | |
| 5,504,575 A | 4/1996 | Stafford | |
| 5,537,303 A | 7/1996 | Stacy | |
| 5,579,105 A | 11/1996 | Belton et al. | |
| 5,586,442 A | 12/1996 | Nicodemus | |
| 5,592,327 A | 1/1997 | Gabl et al. | |
| 5,686,722 A | 11/1997 | Dubois et al. | |
| 5,691,886 A | 11/1997 | Stacy | |
| 5,748,308 A | 5/1998 | Lindberg et al. | |
| 5,991,460 A | 11/1999 | Mitchell | |
| 6,011,640 A | 1/2000 | Hutton | |
| 6,018,402 A | 1/2000 | Campbell et al. | |
| 6,101,034 A | 8/2000 | Cox et al. | |
| 6,128,078 A | 10/2000 | Fateley | |
| 6,271,917 B1 | 8/2001 | Hagler | |
| 6,388,794 B2 | 5/2002 | Hagler | |
| 6,762,833 B2 | 7/2004 | Hagler | |
| 6,859,275 B2 | 2/2005 | Fateley et al. | |
| 6,897,952 B1 | 5/2005 | Hagler | |
| 6,982,788 B2 | 1/2006 | Hagler | |
| 6,995,840 B2 | 2/2006 | Hagler | |
| 6,999,165 B2 | 2/2006 | Hagler | |
| 2004/0021078 A1 | 2/2004 | Hagler | |

FOREIGN PATENT DOCUMENTS

WO     WO97/31245 A1     8/1997

OTHER PUBLICATIONS

Golay, M., "Multi-Slip Spectrometry," Journal of the Optical Society of America, Jun. 1949, pp. 437-444, vol. 39, No. 6.

Grainger, J. F. et al., "A Multiplex Grating Spectrometer," Journal de Physique, Colloque C2, Mars-Avril 1967, pp. C2-44-C2-52, supplemental au No. 3-4, Tome 28.

International Search Report PCT/US99/14446, Jan. 11, 2000, 7 pages.

International Search Report, PCT/US03/07369, Oct. 27, 2003, 6 pages.

Search Report mailed Oct. 21, 1999, PCT/US99/14446, 6 pages.

International Preliminary Examination Report, PCT/US99/14446, Sep. 14, 2000, 31 pages.

Written Opinion, PCT/US99/14446, 6 pages.

Written Opinion, PCT/US03/07369, Sep. 4, 2004, 4 pages.

International Search Report and Written Opinion, PCT/US05/22959, Aug. 1, 2006, 7 pages.

ENCODER SPECTROGRAPH FOR ANALYZING RADIATION USING SPATIAL MODULATION OF RADIATION DISPERSED BY WAVELENGTH

CROSS REFERENCE TO RELATED APPLICATIONS

This application claims the benefit of U.S. Provisional Application No. 60/583,834, filed Jun. 28, 2004, and U.S. Provisional Application No. 60/637,148, filed Dec. 16, 2004, each of which is incorporated by reference in its entirety.

BACKGROUND

1. Field of the Invention

This invention relates in general to radiation spectrum analyzers and radiation image analyzers, and in particular, to radiation analyzers and encoders that use spatial modulation of radiation dispersed by wavelength.

2. Background of the Invention

Radiation spectral analysis is presently carried out in a number of ways. Dispersive and Fourier transform based analyzers are for high resolution and can be used for many different applications so that they are more versatile than existing application-specific instruments and procedures. While these analyzers offer superior spectral performance, they tend to be expensive, large, heavy and non-portable. For most applications, these instruments offer a spectral resolution that is largely unnecessary. Many analytical computations can be made using relatively few spectral measurements. The processing of the additional, unnecessary optical data reduces the speed and compromises the photometric accuracy of these instruments.

In contrast, a non-dispersive approach to spectral analysis employs a radiation source filtered by one or more bandpass to provide input to a specific analytical function. The bandpass filters are used to select one or more specific spectral components, which are characterized by a center wavelength and bandwidth. One of the principal advantages of the non-dispersive approach is the ability to individually specify the center wavelength and bandwidth of the bandpass filters to optimize the instrument for a particular application. However, if the analytical function requires a significant number of bandpass filters, the system's signal-to-noise ratio is reduced as the total energy measured in a given filter over time is inversely related to the number of filters. Furthermore, if a spectrum analyzer using this approach is configured for a first application, the filters used in the device may have to be replaced, or the number of filters changed, to adapt the analyzer to a second application. As a consequence, the non-dispersive approach has clear limitations in adaptability and in the number of spectral components that can be analyzed.

Another type of optical spectrum analyzer is the Hadamard spectrometer, which is best described as a hybrid between dispersive and non-dispersive instruments. The Hadamard spectrometer includes a spatial radiation modulator, comprising a disc made of an opaque material with slots therein that reflect or transmit radiation, where the slots have uniform transmittance or reflectance. A radiation beam is dispersed according to wavelength onto the disc and the slots are selectively spaced at different radii from the axis to form a number of different optical channels for detecting corresponding spectral components of the beam. The disc is rotated about the axis and the slots selectively encode the corresponding spectral components with a binary amplitude modulation. The encoded beam is then directed to a detector. To differentiate the intensity of the spectral component transmitted or reflected by one slot from that of another, the disc is sequentially stepped through a specific number of steps, each step comprising a binary pattern of open or closed optical channels that defines one equation in a system of simultaneous equations for the amplitudes of the spectral components. This set of simultaneous equations is then solved to yield the intensity for each channel prior to any specific analytical function.

Not only is this approach time consuming, it is prone to errors. For example, as a direct consequence of the binary encoding approach, there is no mechanism by which one can recover the actual signal levels if any one of the signal levels changes significantly over the period of rotation. It should be noted that the system of equation can be simplified if the slots are patterned such that the radiation is transmitted or blocked one spectral component at a time (e.g., a filter-wheel photometer). However, this approach changes the optical duty cycle of each of the spectral components from its optimum value of 50%, thereby degrading the signal-to-noise ratio. Finally, if a Hadamard analyzer is configured for a first application and the number of slots is changed to adapt the analyzer to a second application, the data acquisition and decoding algorithms must be changed as well. This significantly limits the instrument's adaptability.

None of the existing approaches is entirely satisfactory. Therefore, it is desirable to provide improved spectrum and image analyzers where the above-noted disadvantages are avoided or significantly diminished, and where the encoding, data acquisition and decoding are both generalized and significantly simplified.

SUMMARY OF THE INVENTION

Embodiments of the invention provide many advantages over existing radiation analyzers. In some embodiments, an encoder spectrograph employs a double-crossover optics system that allows for a highly compact encoder design. The encoder spectrograph can be made even more compact by increasing the symmetry of the optics system, for example using optics having vertices in a common plane. The encoder spectrograph may have a dual optics system that allows for encoding of two radiation beams simultaneously, thus facilitating a number of useful applications. Various additional improvements enable an encoder spectrograph having a small size and increased performance relative to previous systems.

In one embodiment, an encoder spectrograph encodes a received incident radiation beam using spatial modulation of the received beam dispersed by wavelength. A first optics disperses the received incident beam of radiation by wavelength and redirects the dispersed beam across the incident beam to form an image dispersed by wavelength along a dispersion axis. The first optics may comprise a concave diffraction grating and a crossover focusing reflector. A spatial light modulator is positioned to receive the dispersed image on a surface of the modulator. The spatial light modulator modulates the intensity of the dispersed image according to the position along the dispersion axis, thereby providing an encoded beam. A second optics collects the encoded beam from the spatial light modulator, redirects the encoded beam across the dispersed beam, and focuses the encoded beam to form a substantially overlapping image. In one embodiment, the second optics comprises a crossover fast collection optic and a detector lens. A detector element, positioned to receive the overlapping image, produces a signal representative of the encoded beam.

As described, in one embodiment, the path of the received beam crosses itself twice before reaching the detector. This double-crossover design allows the encoder spectrograph to be relatively small. In addition, the optics used to disperse, redirect, and collect or focus the beam at various stages in the optical path can be highly symmetric. The symmetry of the design further allows for a simpler and more compact encoder. Two or more of the optics components in the design may be mounted using a single mounting structure, thereby facilitating the manufacture of the encoder and the alignment of the optics in the device. In one embodiment, the diffraction grating is separately mounted, allowing for the removal of the grating and the installation of another grating, e.g., a grating designed for another application.

Other embodiments of the instrument comprise a dual encoder spectrograph that encodes separate beams using the same modulator, which may be applied in a number of applications. For example, a single instrument may employ two spectrographs operating in different spectral regions (e.g., near-infrared (NIR), mid-infrared (MIR), and/or untraviolet (UV)) but mounted onto a single encoder. In one embodiment, a sampling interface is used with two sampling sub-systems optimized for liquid (and/or solid) and gas (and/or vapor) phase samples. Each sampling sub-system can be interfaced with one of the spectrographs to enable the simultaneous analysis of samples having both liquid and solid, liquid and gas or vapor, and/or solid and gas constituents.

In another example, a single instrument employing two spectrographs is interfaced with two sampling sub-systems: an attenuated total reflectance (ATR) system for analyzing solids and/or liquids, and a gas cell for analyzing ambient air. In this manner, a first responder can analyze samples at the scene of an incident while simultaneously monitoring the ambient environment for potential hazards using a single instrument.

In another embodiment, to minimize phase error and maximize orthogonality, an in-situ phase analysis based on prime-number encoded components is used. The in-situ phases analysis may be performed using sine-only or cosine-only modulations to determine the phase of the encoded signals. In this way, the user can maximize the orthogonality of sine and cosine components having the same modulation frequency.

In another embodiment, the encoder spectrograph analyzes a continuous stream of spectra acquired during a calibration training mode. The spectrograph-encoder analyzer automatically logs those unique spectra required to build a calibration model, also called calibration training spectra. This enables a user to identify and quantify analytes by analyzing unknown spectra by acquiring the proper reference spectra required for the underlying calibration.

In another embodiment, a user can "tag" spectra with analyte species and concentration information, possibly during the collection of the calibration training spectra. One or more selected unique calibration training spectra can be compared with spectra from a spectral library or other database for further verification of assigned tags. In this way, users can share information and compare results between two or more instruments.

DETAILED DESCRIPTION OF THE PREFERRED EMBODIMENTS

Disclosed herein are embodiments of an encoder spectrograph and related systems, subsystems, and applications for analyzing radiation from a sample. In various embodiments, an encoder spectrograph uses a spatial light modulator to encode dispersed radiation. The spatial light modulator for the encoder spectrograph may be implemented by a reflective modulator disc having a pattern of radiation intensity filters. Generally, embodiments of radiation analyzers and encoders that use spatial modulation of radiation dispersed by wavelength are described in U.S. Pat. No. 6,271,917, U.S. patent application Ser. No. 09/848,614, and U.S. patent application Ser. No. 10/384,374, each of which is incorporated by reference in its entirety. In one embodiment in accordance with the present invention, an encoder spectrograph comprises a Littrow-mount double-crossover optical system, which provides a number of advantages over previous designs.

Optical System for Encoder Spectrograph

Figure 1:
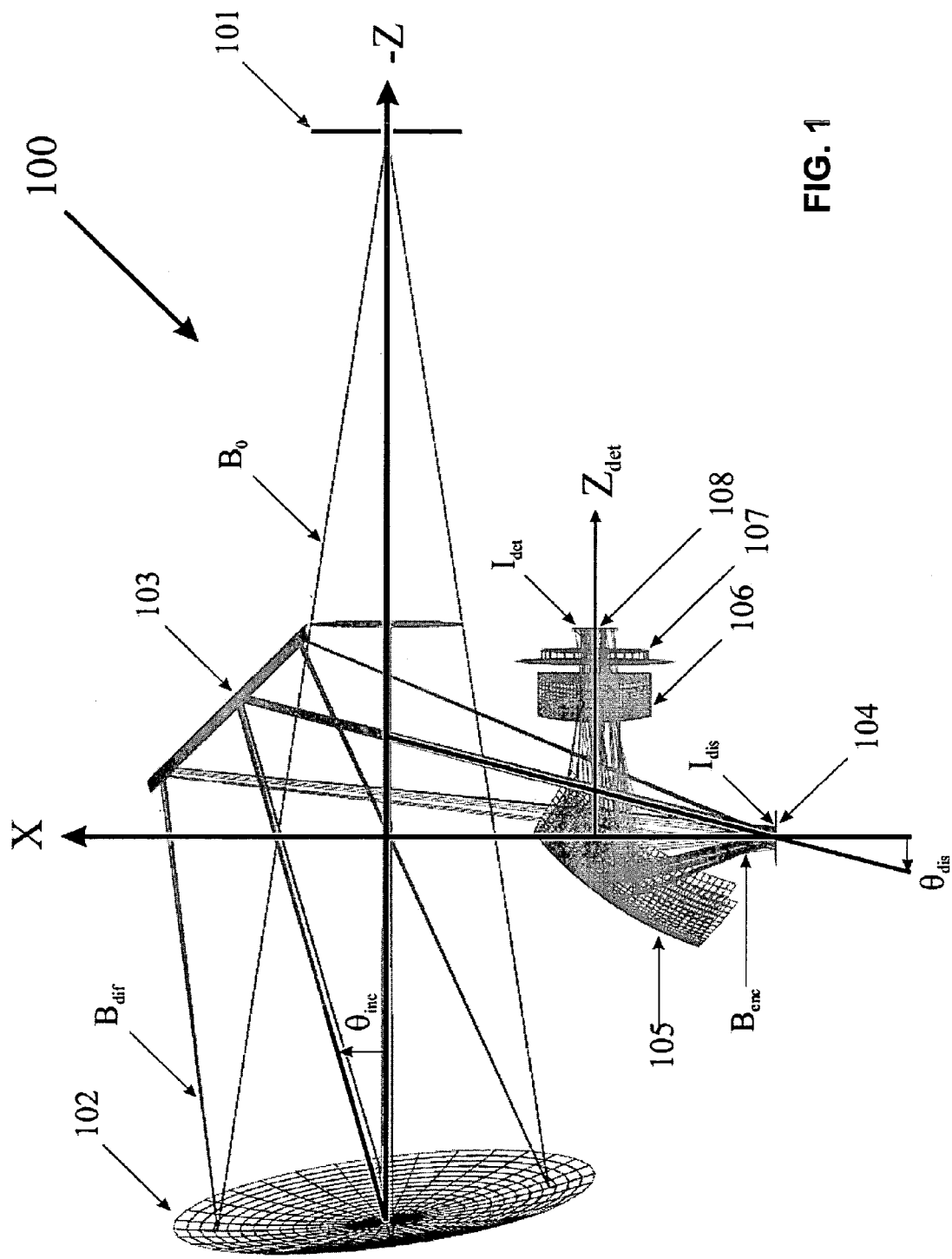
FIG. 1 is a schematic side view of an optical system for an encoder spectrograph, in accordance with an embodiment of the invention.

FIG. 1 is a side view (i.e., in the global XZ-plane) of an optical system for an encoder spectrograph 100, in accordance with one embodiment of the invention. The optical system comprises an entrance aperture 101, a concave diffraction grating 102, a crossover focusing reflector 103, a spatial light modulator 104, a crossover fast collection optic 105, a detector lens 106, a detector window 107, and a detector element 108. Additional elements can be included to improve performance or to accommodate different radiation sources, sample accessories, spatial light modulators, and/or radiation detectors. As shown in FIG. 1, the entrance aperture 101 is located in a plane substantially parallel to the global XY-plane, and the normal to the entrance aperture 101 and the normal to the detector element 108 are parallel.

As depicted in FIG. 1, an incident radiation beam $B_0$ is launched through entrance aperture 101 along the Z-axis and illuminates concave diffraction grating 102. The diffracted radiation beam $B_{dif}$ is directed toward crossover focusing reflector 103, which redirects and focuses $B_{dif}$ to form dispersed image $I_{dis}$ on the surface of a spatial light modulator 104. The dispersed image $I_{dis}$ is encoded by the encoder 104 to provide an encoded radiation beam $B_{enc}$. The encoded radiation beam $B_{enc}$ is collected, focused and redirected by crossover fast collection optic 105 toward a detector lens

106. The detector lens 106 provides additional focusing to project the encoded radiation beam $B_{enc}$ through a detector lens 107 and form a substantially overlapping image $I_{det}$ on the surface of detector element 108, as described in U.S. patent application Ser. No. 10/384,374.

In one embodiment, the concave diffraction grating 102 has an illuminated diameter of 34 mm and a radius of curvature $R_0$ of approximately 100 mm, resulting in an F/# of approximately 1.5. Other parameters can be chosen for the concave diffraction grating 102 for various applications, within the scope of the invention. The concave diffraction grating 102 may have variable line (groove) spacing or holographic etching to minimize the number of optical elements. In the embodiment shown in FIG. 1, the concave diffraction grating 102 has a biconic substrate and a variable line spacing function that is modeled as a polynomial in both the local X and Y-axes. Other embodiments incorporating a diffraction grating 102 comprising torroidal, aspherical, spherical or plane mirror surfaces with ruled or holographic etched patterns are within the scope of the invention.

As shown, the concave diffraction grating 102 is rotated relative to the plane of entrance aperture 101. The rotation is about an axis through its center parallel to the Y-axis (i.e., inclination), and about an axis through its center parallel to the X-axis (i.e., auto collimation, shown in FIG. 2).

The radiation diffracted by the diffraction grating 102 (diffracted beam $B_{dif}$) is directed toward a crossover focusing reflector 103, preferably at an inclination angle $\theta_{inc}$. From a sequential ray tracing perspective, the value for inclination angle $\theta_{inc}$ that minimizes aberration in the dispersed image is zero, but that configuration would result in an unphysical design where the crossover focusing reflector 103 obstructs incident radiation beam $B_0$. In one embodiment, therefore, the value for inclination angle $\theta_{inc}$ is optimized to minimize aberrations and maximize throughput. The inclination angle $\theta_{inc}$ may be optimized in one way by selecting the inclination angle $\theta_{inc}$ that just clears the crossover focusing reflector 103 out of the incident beam path. In one example, this inclination angle $\theta_{inc}$ is approximately 7 to 8 degrees.

The crossover focusing reflector 103 directs the diffracted radiation beam $B_{dif}$ across incident radiation beam $B_0$ to form a dispersed image $I_{dis}$ on the surface of a reflective spatial light modulator 104. The reflector 103 also provides additional focusing power to enable concave grating 102 to have a substrate shape that minimizes aberration in the dispersed image and maximized system throughput. In one embodiment, the reflector 103 has a cylindrical surface with an axis in the XZ-plane and a radius of curvature of roughly $4R_0$ to provide additional focusing power along the dispersion axis. Other parameters may be selected in view of the trade off between the radius of curvature of the focusing reflector 103 and the corresponding radius of curvature of the diffraction grating 102, due to a reduction in the magnitude of the diffraction angles at the extremes of the dispersed image. For example, the crossover focusing reflector 103 may be modeled as a cylindrical surface with axis in the YZ-plane and as a biconic or torroid. Other embodiments may incorporate a crossover focusing reflector 103 that comprises aspherical, spherical, or planar mirror surfaces.

Figure 2:
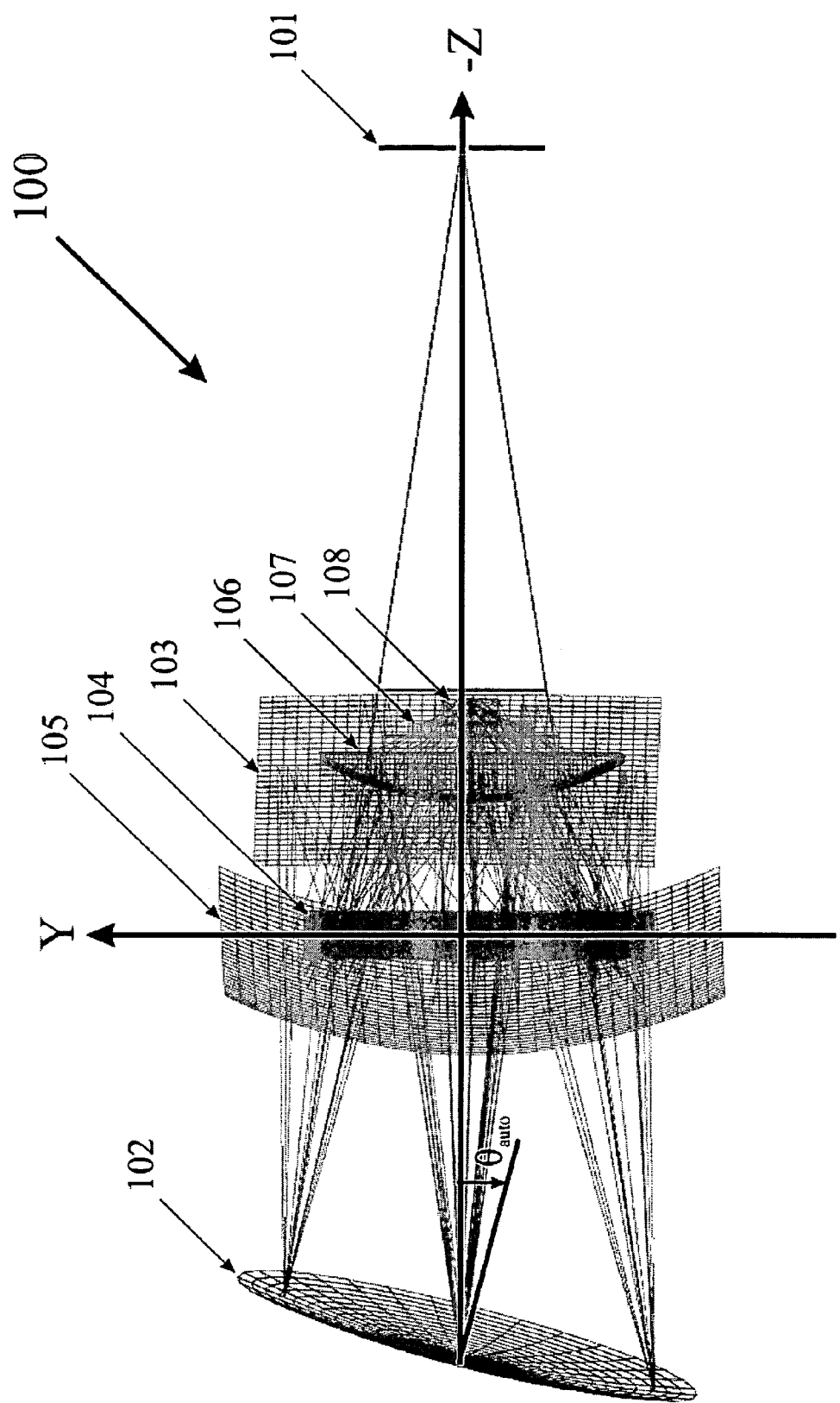
FIG. 2 is a schematic top view of the optical system for the encoder spectrograph shown in FIG. 1, in accordance with an embodiment of the invention.

The spatial light modulator 104 is located in a plane that is substantially parallel to the global YZ-plane, as defined in FIGS. 1 and 2. In one embodiment, the spatial light modulator 104 for the encoder spectrograph 100 may comprise a rotating encoder disc patterned, as described in U.S. patent application Ser. No. 10/384,374. In another embodiment, the spatial light modulator 104 may comprise other types of spatial light modulators, including addressable LCDs and MEMS devices. In addition, optical elements 101 through 103 may also be used with a conventional detector array.

In one embodiment, the encoder pattern is part of the optimized optical system, and the radial position and radial width of the annular regions encompassing the radiation filters on the spatial light modulator 104 can be optimized along with the other optical elements to maximize performance. Because of the flexibility in specifying the size, shape, and location of the radiation filters, the spatial light modulator 104 can be optimized to compensate for artifacts introduced by holographic grating manufacturing methods, e.g., non-parallel grooves. For a given holographic grating, an encoder pattern can be designed to improve system performance significantly (e.g., the details of the radiation filters or the configuration of LCDs or MEMS elements).

Preferably, the holographic grating and the encoder pattern are designed in consideration of the other to exploit annular shaped spectral sub-images in the dispersed image, which in turn minimizes other aberrations or throughput limitations in the system.

In the embodiment shown, the diffracted radiation beam $B_{dif}$ has an angle of incidence in the XZ-plane of roughly 15 degrees with respect to the surface of the modulator 104. This angle of incidence enables the positioning of a collection optic 105. The modulator 104 encodes the dispersed image $I_{dis}$ by modulating reflectance to provide an encoded beam $B_{enc}$. The encoded beam $B_{enc}$ is collected by the collection optic 105 and directed across the diffracted radiation beam $B_{dif}$ onto the surface of a detector lens 106. In one embodiment, the collection optic 105 is modeled as a biconic, an asphere, or as a torroid surface (e.g., using ZEMAX® optical design software); however, other types of optics can be used to collect the encoded beam $B_{enc}$. Other embodiments may incorporate a collection optic 105 that comprises aspherical, spherical, or planar mirror surfaces.

Encoded radiation beam $B_{enc}$ is focused by the collection optic 105 and the detector lens 106 through a detector window 107 and onto the surface of a detector element 108 to form detector image $I_{det}$. Although the surface of the detector lens 106 may be strictly spherical to minimize cost, the aperture of the detector lens 106 can be cropped to prevent a non-illuminated portion of the lens from obstructing incident radiation beam $B_0$. To crop the detector lens 106, it may be notched, cut, or ground flat along an edge. The cropping also serves to prevent mechanical interference with spatial light modulator 104. In the embodiment shown in FIG. 1, the detector lens 106 is a plano-convex design with a spherical surface. Other embodiments may incorporate a detector lens 106 that has one or more biconic, torroidal, or aspherical surfaces (convex or concave).

FIG. 2 shows a top view of the encoder spectrograph 100 of FIG. 1, illustrating the relationship between the auto collimation angle $\theta_{inc}$ and the dispersed image $I_{dis}$ on the surface of the modulator 104. FIG. 2 shows a high degree of beam symmetry—approximate mirror symmetry—through the XZ-plane, which simplifies the placement and fabrication of the optical components (e.g., the lens 106 is spherically symmetric). As shown in FIG. 2, the centers of the optical elements are each substantially in the global XY-plane.

Figure 3:
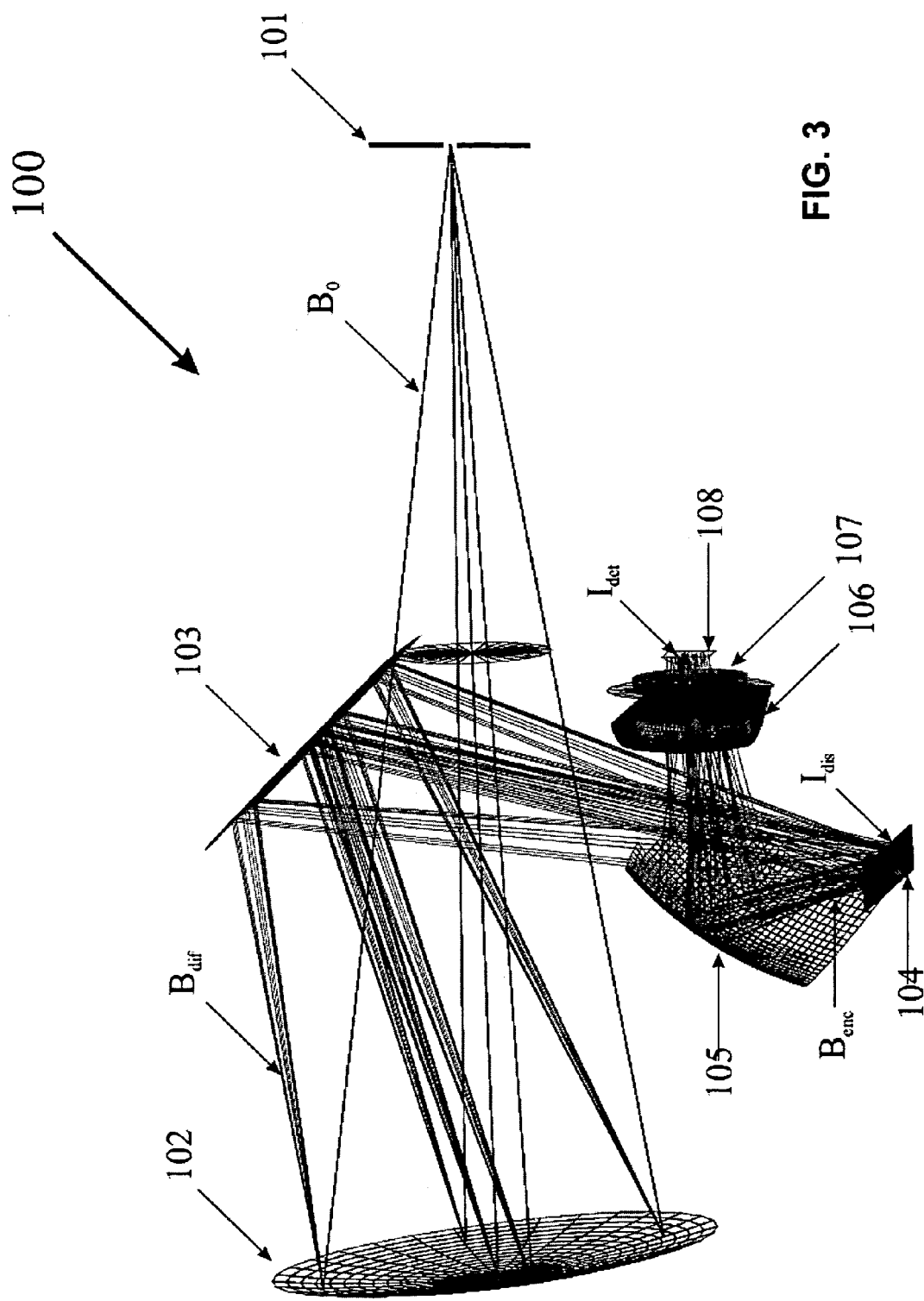
FIG. 3 is a schematic perspective view of the optical system for the encoder spectrograph shown in FIG. 1, in accordance with an embodiment of the invention.

FIG. 3 is a perspective view of the prototype system described in FIG. 1, illustrating the three-dimensional relationship between the optical components and the crossing beam paths. Preferably, the auto collimation angle $\theta_{inc}$ and the grating pattern (e.g., holographic etching or ruled lines/grooves) are optimized (1) to project the correct spectral range over the surface of the modulator 104, (2) to maximize spectral purity in the encoded components, and (3) to maximize the collection efficiency of post-encoder optics 105 through 108. In one embodiment, the dispersed image spans about the 3 to 5-micron spectral range, the nominal line frequency of grating 102 is about 110 g/mm, and the auto collimation angle is about 13-14 degrees.

In one embodiment, the optical surfaces of the optical elements are optimized to maximize the spectral resolution of the encoded dispersed image $I_{dis}$ and to maximize the overlap of the encoded spectral components on detector element 108 to produce detector image $I_{det}$. In various embodiments, the optics system for the encoder spectrograph 100 is optimized using the merit function design strategies, as detailed in U.S. patent application Ser. No. 10/384,374.

In an example embodiment, the dispersed image $I_{dis}$ is roughly 2 mm in width and 25.4 mm in length, the detector element 108 is 3 mm by 3 mm, and the optical path between the modulator 104 and the detector element 108 is roughly 40 mm. The optical system of the encoder spectrograph 100 occupies a space of roughly 110 mm by 50 mm by 60 mm, along the Z, Y, and X-axes, respectively. The radius of the encoder disc 104 is slightly greater than the focal length of the grating 102, thereby enabling a very efficient use of space, e.g., in and around the spindle motor and encoder disc. The minimum spectral efficiency is greater than 80% at the encoder and greater than 70% for 128 spectral components encoded in the 3 to 5-micron spectral range.

As described in U.S. patent application Ser. No. 10/384,374, the distance of the optical path between the reflective spatial light modulator 104 and the detector element 108 is preferably designed to be as short as possible for a given detector element size (e.g., preferably less than 45 mm for a 3 mm by 3 mm detector element). A post-optic, defined by optical components 105 through 108, is a variation of and can be replaced by a short-path post encoder optics described in U.S. patent application Ser. No. 10/384,374. One advantage of the post-collection optic shown in FIGS. 1-3 is the elimination of one of the reflective surfaces described in U.S. patent application Ser. No. 10/384,374. The fast collection optic 105 can be modeled as a biconic, a torroid, and/or as an apertured asphere. In one embodiment, a biconic with additional aspherical terms added to the local y-radius of curvature is used.

In one embodiment, the encoder spectrograph 100 is designed by approximating the shape of the intercept of the annular radiation filters and the dispersed image as rectangular bins to allow the axis of the dispersed image to be aligned parallel or anti-parallel to the radius of an encoder disc. This feature enables the user to reverse the order of wavelength versus encoder radius by moving the spectrograph to the opposite side of the encoder disc. Since the modulation frequencies generally increase with increasing encoder disc radius, this flexibility allows a designer to select whether the highest modulation frequencies correspond to the longest or the shortest wavelengths. This in turn allows the designer to minimize the effects from residual interferences from imperfect orthogonal encoding functions (e.g., integer harmonics) by encoding critical spectral regions at lower frequencies. In the 3 to 5-micron spectral range, for example, one could encode the $CO_2$ spectral region at higher frequencies to minimize the residual interference effects of dynamically varying $CO_2$ concentrations on the encoded hydrocarbon spectral components.

The use of rectangular-shaped bins also enables an instrument incorporating a single encoder and twin spectrographs with entrance apertures on the same side of the housing. For example, the each spectrograph can be coupled to its own sample cell located on the same side of the instrument. Different length sample cells can be used to maximize sensitivity and minimize absorption saturation for applications involving chemical mixtures that have a wide range of constituent concentrations, e.g., natural gas. This enables the real-time spectral analysis of a single in-line sample path with two different length sample cells and/or two distinct spectral ranges.

The encoder spectrograph 100 can be designed such that the centers of the individual optical components are located in a substantially common plane parallel to a perpendicular bisector of the midpoint of the dispersed image $I_{dis}$. The encoder spectrograph 100 may also be designed to minimize its footprint, particularly along the dispersion axis. The use of a double-crossover beam path and component symmetries help to reduce the encoder's footprint. The position of the concave diffraction grating 102 may located behind the position of encoder spindle motor to enable the dispersed image $I_{dis}$ to be located as close to the rotational axis as possible. In this manner, instrument designs employing smaller encoder discs are possible.

In one embodiment, the grating 102 is mounted in an inclined Littrow auto-collimation configuration so that the diffraction angles are symmetrical about the midpoint of the dispersed image $I_{dis}$. This helps to minimize aberrations or distortions to the dispersed image $I_{dis}$ and to maximize the collection efficiency of the post-encoder optics (components 105 through 108). The Littrow auto-collimation mounting of the grating 102 makes the encoder spectrograph 100 highly symmetrical about the midpoint of the dispersed image $I_{dis}$ and thereby enables the grating 102 to be located on either side of a spindle motor used to rotate the encoder 104.

The inclination angle $\theta_{inc}$ of the diffraction grating 102 may be defined as a rotation about an axis that passes through the origin of the diffraction grating 102 that is parallel to the nominal dispersion axis (e.g., the radial axis of the encoder disc 104). The optical throughput of the encoder spectrograph 100 is normally constrained by the inclination angle $\theta_{inc}$ of the concave diffraction grating 102 and the corresponding placements of the crossover focusing reflector 103 and the detector lens 106. These components are preferably arranged to optimize the tradeoff between throughput and aberrations in the dispersed image. The inclination angle $\theta_{inc}$ of the diffraction grating 102 can be optimized to maximize throughput and minimize aberrations. Preferably, the crossover focusing reflector 103 and detector lens 106 are notched or otherwise shaped to maximize optical throughput.

In one embodiment, the encoder spectrograph 100 includes a single bracket to hold and position the crossover focusing reflector 103, the fast collection optic 105, the detector lens 106, the detector window 107, and the detector element 108. This simplifies assembly of the system and facilitates alignment of the optical components. In addition, the single bracket construction provides a more stable and thermally predictable alignment. Preferably, the crossover focusing reflector 103, the fast collection optic 105, and the mounting provisions for the lens 106 are combined into a single injection-molded optic. To create the reflective metallic surfaces for the reflectors 103 and 105, a metal may be evaporated on the injection-molded optic by placing it on a rotating chuck in an evaporation chamber.

In one embodiment, the entrance axis of the encoder spectrograph 100 (i.e., the normal to the entrance aperture 101) and the detector axis (i.e., the normal to the surface of the detector element 108) are parallel to each other and to the plane of the spatial light modulator 104. In addition, the entrance aperture 101 is perpendicular to the side of the enclosure. This configuration enables the use of an enclosure with "straight-in" optical coupling to simplify the integration and alignment of sampling accessories. Alternately, folding mirrors can be introduced to enable other configurations for the entrance aperture and the detector plane.

Non-lineal and nonlinear models for the dispersed image may be introduced to minimize optical aberrations and maximize throughput. Because of the flexibility in defining the annular regions encompassing the encoding tracks, the radial position and the radial width of the encoding tracks can be varied to compensate for nonlinearities (e.g., compressions and expansions along the radial axis). The phases of the encoding patterns or the decoding algorithm can be varied to compensate for variations in the position of the spectral centroids along the azimuthal axis within an annular region.

Holographic Grating

Because of the effects of the non-zero inclination angle $\theta_{inc}$, illustrated in FIG. 1, improved efficiency and spectral purity may be obtained when the holographic recording coordinates are located out of a plane containing the surface normal at the center of grating substrate 102. In one embodiment, this is facilitated by creating a ZEMAX® compatible User Defined Surface that constrained ZEMAX® Hologram Type 1 coordinates to lie in a plane that is parallel to the Y-axis of FIG. 1. The highest efficiency and spectral purity may be obtained when the holographic recording coordinates are located in the plane shown in FIG. 2 that makes an angle $\theta_{inc}$ relative to the surface normal at the center of grating substrate 102.

In a standard detector array instrument, the pitch between detector elements is fixed and is typically uniform. Spectrograph designs employing detector arrays are therefore optimized to provide a substantially linear relationship between wavelength and the distance between detector elements along the detector array axis (i.e., a linear dispersion function). In an embodiment of the invention, improved efficiency and spectral purity are obtained by incorporating radiation filters that have non-equal widths and are centered at non-equal intervals along the encoding axis of the modulator 104, the Y-axis in FIG. 2. This corresponds to a non-linear relationship between wavelength and the distance between encoding tracks along the encoding axis (i.e., a non-linear dispersion function). In addition, the efficiency and spectral purity of the system can be optimized for constant energy separation and resolution, as well as arbitrary configurations of spectral components.

In one embodiment, the optical system is optimized using a multi-order polynomial in the position along the Y-axis of FIG. 2 to define the position and widths of the annular regions bounding the radiation filters. The highest efficiency and spectral purity may be obtained when the holographic recording coordinates are optimized along (simultaneously) with the multi-order polynomial coefficients defining the position and widths of the encoding tracks (encoding bins) along the Y-axis of FIG. 2.

In another embodiment, the diffraction grating 102 is optimized to exploit the true annular-shaped intercept between the dispersed image $I_{dis}$ and the concentric radiation filters on the encoder disc 104. The overlap of an annular region of radial with $w_0$ located at radius $r_0$ with a rectangle of width $w_0$ and length $l_0$ is only 100% in the limit of infinite radius $r_0$. Therefore, creating dispersed images where spectral components occupy annular bins enables the use of an encoder disc with a smaller radius without a significant loss in spectral resolution.

Practical Embodiments for Optical Elements

In practical embodiments of the encoder spectrograph 100, it may be useful to consider optical elements (e.g., mirrors, grating substrates, and lenses) that have surfaces (i.e., the surface sag, not to be confused with the shape of the aperture) that are rotationally symmetric as opposed to biconic or torroidal surfaces, and lenses that are spherical rather than aspherical. Although embodiments of the encoder spectrograph 100 incorporating non-rotationally symmetric optical components and aspherical lenses may demonstrate higher optical performance, cost and manufacturability considerations may drive the decision for what is best suited for a given application. In one practical embodiment of encoder spectrograph 100, the diffraction grating 102 is formed using a holographic etching process on a spherical substrate having a radius of curvature of roughly 100 mm, the crossover-focusing optic 103 is an asphere having a nominal radius of curvature of roughly 400 mm, the crossover fast collection optic 105 is an asphere with a nominal radius of curvature of roughly 30 mm, and the detector lens 106 has a spherical surface with a nominal radius of curvature of 30 mm when fabricated from silicon or other material with a similar index of refraction.

Mounting Structure for Encoder Spectrograph

Figure 4:
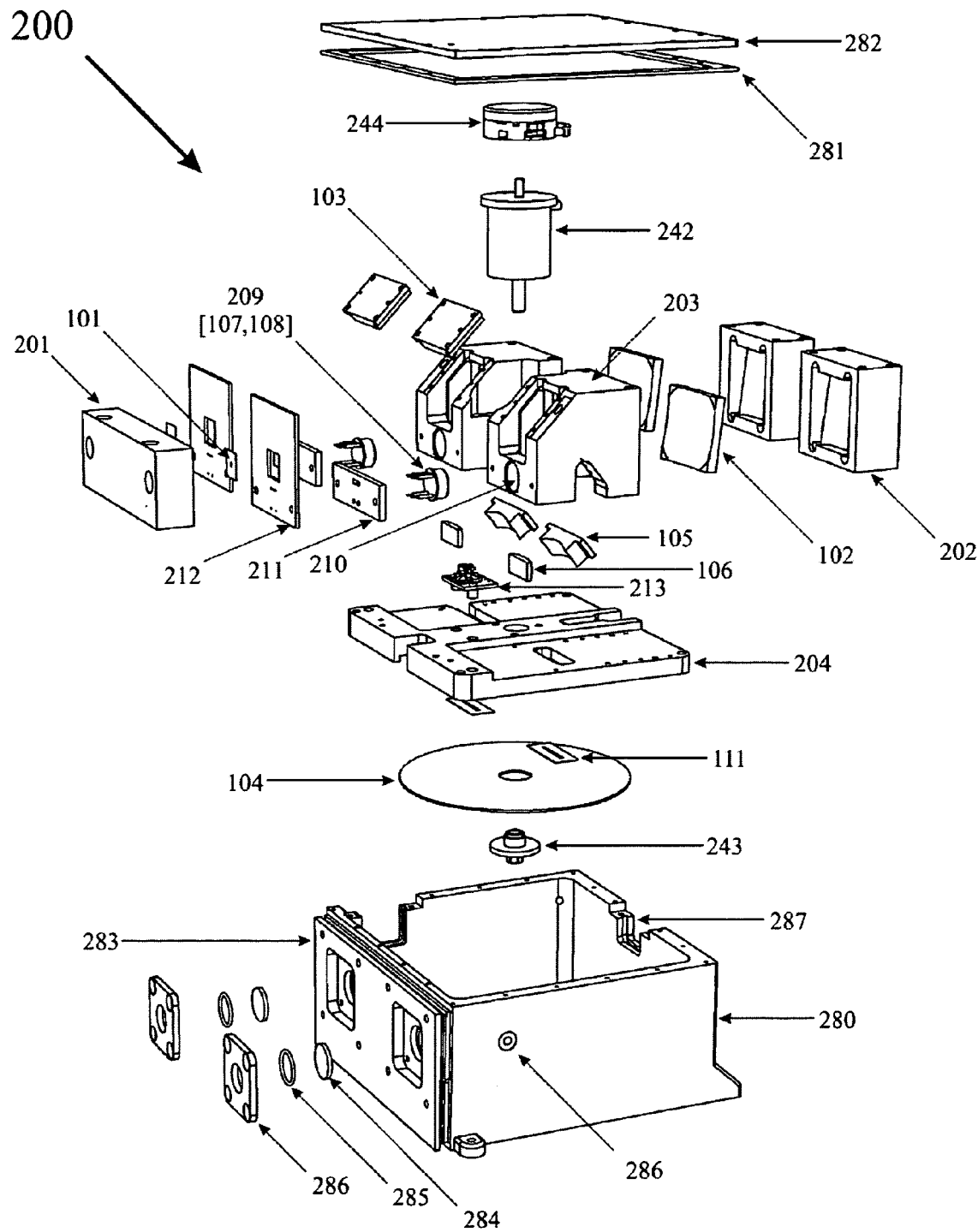
FIG. 4 is an assembly view of a double-crossover encoder spectrograph, in accordance with an embodiment of the invention.
Figure 5:
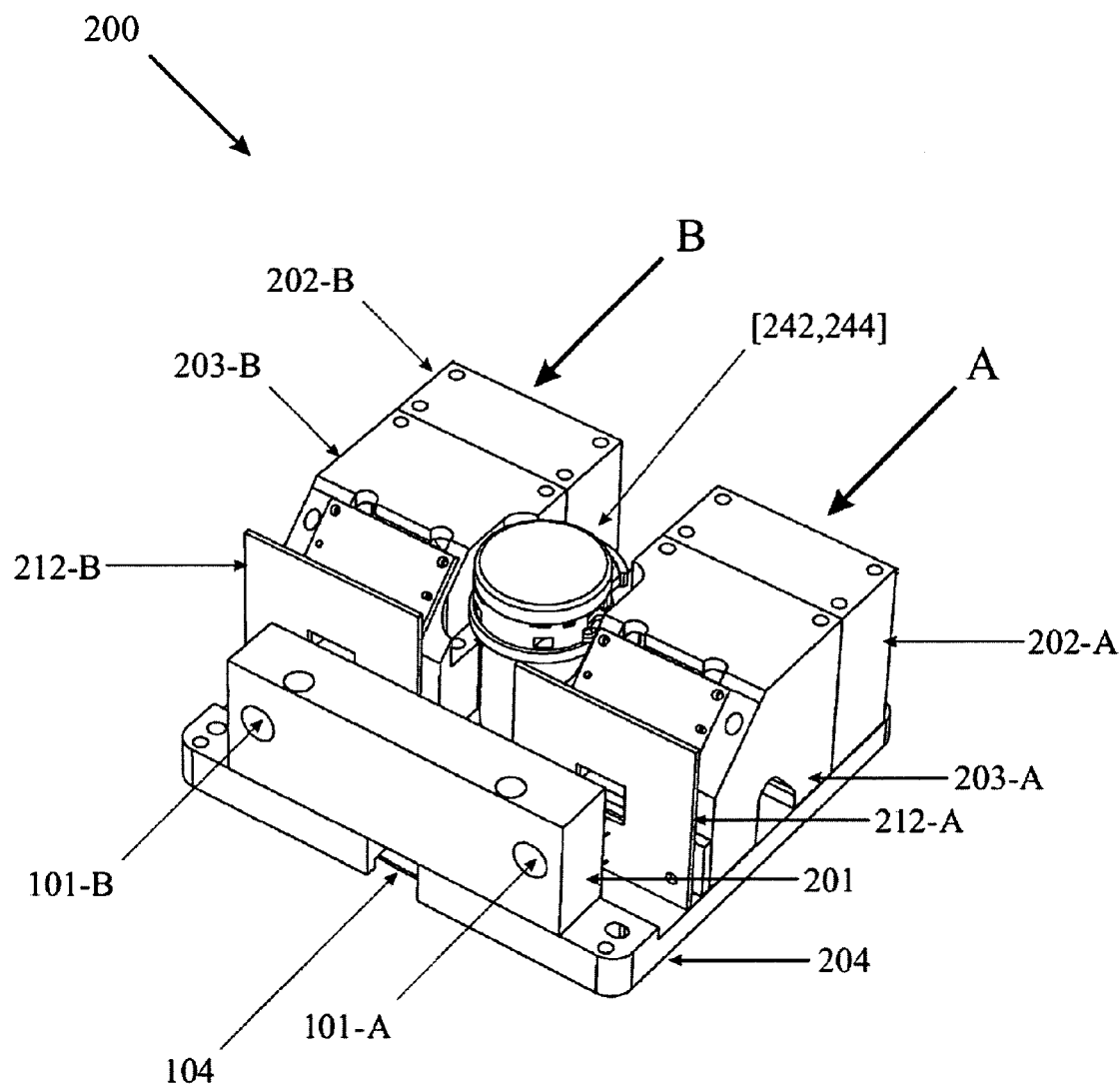
FIG. 5 is a perspective view of the double-crossover encoder spectrograph shown in FIG. 4, in accordance with an embodiment of the invention.
Figure 6:
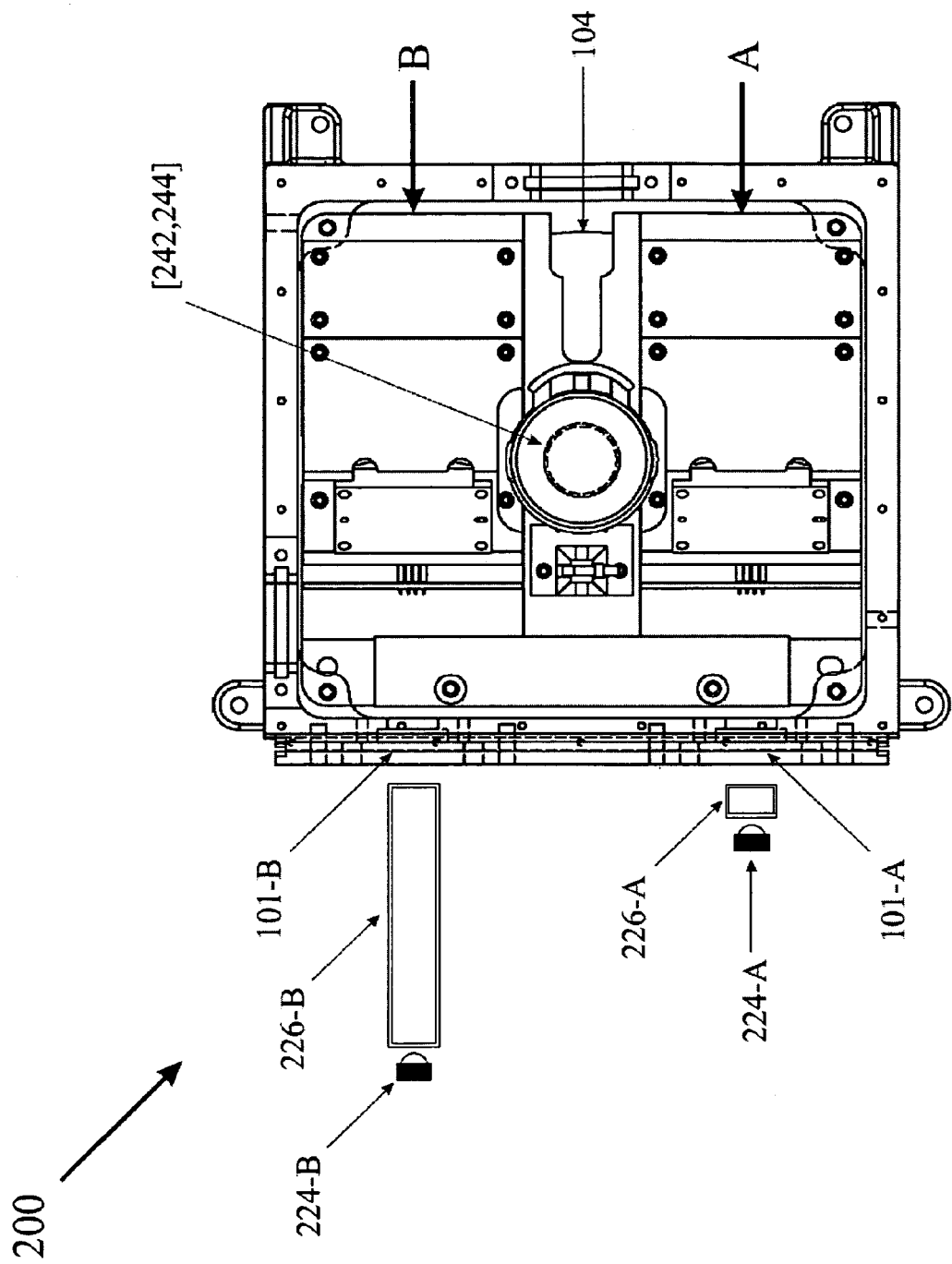
FIG. 6 is a plan view of the double-crossover encoder spectrograph shown in FIG. 4, in accordance with an embodiment of the invention.

FIG. 4 is an exploded view of a dual-spectrograph encoder 200, in accordance with an embodiment of the invention. In the dual-spectrograph encoder 200, two optical systems are contained within the same device and can be used to encode two independent dispersed images simultaneously using a single encoder disc. Each of the optical systems in the encoder 200 may comprise the double-crossover encoder optics 100 shown in FIGS. 1-3. Accordingly, like reference numerals are used to show the correspondence between the optical components shown in FIGS. 1-3 and the physical components shown in FIGS. 4-6. As illustrated in FIG. 4, an embodiment of a dual-spectrograph encoder 200 implements a modular bracketing architecture to mount the optical components of the encoder spectrograph 100. In FIGS. 5 and 6, the two spectrographs are designated as spectrograph A and spectrograph B. For brevity, one of the spectrographs is described in detail in the description of the modular bracket structure shown exploded in FIG. 4.

The spectrograph 200 receives light through an entrance aperture 101. The entrance aperture 101 comprises an aperture in a thin foil that is mounted onto an entrance aperture bracket 201. In this manner, the optical resolution of the spectrograph 200 can be varied by interchanging foils with different aperture widths. In one embodiment of dual-spectrograph encoder 200, the two aperture foils are different.

The grating 102 is mounted into a grating mount 202. The grating mount 202 includes a mounting surface, receptacle, or cavity that incorporates a compound angle. The compound angle is defined by the inclination angle $\theta_{inc}$ and an auto-collimation angle $\theta_{auto}$, as shown in FIG. 1 and FIG. 2, respectively. In this manner, the system 200 can be configured operate in different spectral ranges by interchanging a system of gratings designed for the same grating mount, but having different grating patterns optimize for different spectral ranges.

An optics bracket 203 includes mounting provisions (including angled surfaces) to hold and position the crossover focusing reflector 103, the fast collection optic 105, and the detector lens 106. The optics bracket 203 also includes a detector insertion receptacle 210 (e.g., a TO-8 compatible) to facilitate the mounting and alignment of the detector 209 (which comprises the detector window 107 and the detector element 108) to the other optical elements. The detector 209 is held into the detector insertion receptacle 210 by a detector backing plate 211, which ensures good thermal contact between the detector 209 and the optics bracket 203. In this manner, the optics bracket 203 adds thermal mass to detector 209 to improve the detector's thermal stability— useful, for example, for infrared applications.

An encoder baseplate 204 provides a common mounting surface to locate precisely the entrance aperture bracket 201, the grating mount 202, the optics bracket 203, and a spindle motor 242 relative to one another. This simplifies alignment and assembly of the system 200. A spindle motor 242 is mounted onto the top side of a baseplate 204 (i.e., the spectrograph side), and the encoder 104 is mounted into a recessed cavity located on the bottom side of encoder baseplate 204 using spindle hub 243. Also shown in FIG. 4 is a rotary encoder 244, which provides signals to synchronize the data acquisition from the detector 209 to the rotation angle of the encoder disc 104.

The optics bracket 203 is mounted onto the encoder baseplate 204 so that the dispersed image $I_{dis}$ is projected through a field-of-view aperture 111 onto the encoder 104. The field-of-view aperture 111 serves to control the illuminated width of the dispersed image along the azimuthal axis of the encoder 104 to match the half-tone area used in the design of the radiation filter as described in U.S. patent application Ser. No. 10/384,374. In addition, field-of-view aperture 111 serves to limit the surface area of the encoder 104 that is visible to the detector 109 to minimize effects of modulated background blackbody radiation on the detector signal.

The location of spindle motor 242, grating mount 202 and optics mount 203 on the top surface of encoder baseplate 204 minimizes or reduces the volume of the encoder spectrograph 200. Other arrangements that locate the spindle motor on the bottom side of encoder baseplate 204 may be employed.

Also shown in FIG. 4 is detector preamplifier printed circuit board 212, which is mounted onto a back detector backing plate 211. The preamplifier printed circuit board 212 includes a clear aperture to allow the incident radiation beam to pass through the plane of a printed circuit board 212 between entrance aperture 101 and grating 102 without obstruction. Other shapes for detector preamplifier printed circuit board 212 used to prevent the obstruction of the incident radiation beam may include different cutouts or apertures. The location and orientation of the printed circuit board 212 can be chosen to mitigate potential sources of noise in the detector signal path by minimizing the distance between the signal leads of the detector 209 and the input to the gain stage of the preamplifier circuit (contained within the printed circuit board 212). Alternatively, the printed circuit board 212 may be located outside of the optical path.

In addition, a temperature sensor 213 may be mounted to the encoder baseplate 204 to provide a measurement of the temperature of the optical system. Preferably, the data provided by the temperature sensor 213 is used in one or more compensation algorithms to correct or provide context to the signals provided by the detector 209.

Also shown in FIG. 4 is the optics enclosure comprising, enclosure housing 280, enclosure coverplate gasket 281, enclosure coverplate 282, enclosure mounting flange 283, enclosure windows 284 (A and B), enclosure window o-rings 285 (A and B), and enclosure window retainer plates 286 (A and B). Encoder baseplate 204 drops into and mounts into the bottom of enclosure housing 280 to provide mechanical and dust protection and an increased thermal mass for the entire optical system. Preferably, the optical enclosure includes provision for gas purging 286, and cable feed-thrus 287 with grommets (not shown) to provide a significantly air-tight enclosure. In this manner, the effects of background chemical concentrations on the uncontrolled path (i.e., the optical path outside of any sampling system) of the optical system can be-mitigated.

In one embodiment, the system 200 is readily configured for different spectral ranges by interchanging the grating 102 and the detector 109 with different gratings and different detectors optimized for different spectral regions. For example, any detector available in a standard package (e.g., a TO-8 package) may be inserted into the detector insertion receptacle 210, and a continuum of spectral regions can be imaged onto the encoder 104 by varying the grating pattern on the substrate of the grating 102. Smaller detector packages can also be made compatible with the detector insertion receptacle 210 using an adaptor ring.

For a system spanning the 2.5 to 5-micron spectral range, the optimized auto-collimation angle ($\theta_{inc}$ in FIG. 1) may be about 10 degrees. The optimized auto-collimation angle is a function of the free spectral range multiplier, which is defined as the ratio of the longest wavelength to the shortest wavelength of the spectral range imaged on the encoder 104 in a given diffraction order. For example, in spectrographs spanning 2.5 to 5 microns, 5 to 10 microns, and 7 to 14 microns, the ratio of the longest wavelength to the shortest is 2×. For a 2× free spectral range multiplier embodiment, the optimized auto-collimation angle is about 10 degrees, whereas for the 3 to 5-micron system described above (5/3× free spectral range multiplier), the optimized auto-collimation angle is about 13 degrees. Preferably, the free spectral range multiplier is less than or equal to 2×. A spectral range of 2.5 to 5.5 microns is chosen to illustrate one embodiment of the invention, and other spectral ranges may be chosen, including 1.375 to 2.75 microns, 2.75 to 5.5 microns, 6 to 12 microns, and 7 to 14 microns.

In a group of instruments spanning different spectral ranges but having a common free spectral range multiplier, a single grating mount 202 can be used to mount the respective different diffraction gratings 102. Modular bracketing may be used to simplify the manufacturing of various spectral analysis instruments based on the encoder spectrograph 200.

Dual Encoder Spectrograph

FIG. 5 illustrates an assembled view of the embodiment of the dual-spectrograph encoder 200 of FIG. 4. In this embodiment, a single encoder disc 104 and a single spindle motor 242 are used to encode dispersed radiation simultaneously using a pair of spectrographs, A and B. In one embodiment, each spectrograph A and B implements the optics system 100 described in FIGS. 1-3. As illustrated, for each spectrograph A and B there is an entrance slit 101-A and 101-B mounted on a common bracket 201. As shown in FIG. 5, each spectrograph A and B of the dual-spectrograph instrument 200 includes a grating mount 202-A and 202-B that secures the corresponding diffraction grating, 102-A and 102-B, respectively, and an optics bracket 203-A and 203-B that holds the corresponding crossover focusing mirror 103-A and 103-B, the crossover fast-collection optic 105-A and 105-B, the detector lens 106-A and 106-B, and the detector 209-A and 209-B, respectively.

As shown in FIG. 5, the spindle motor 242 is located on the same side and sandwiched between the encoder spectrographs A and B. In one embodiment, optics brackets 203-A and 203-B have machined recesses (shown in FIGS. 5 and 6) to enable a closer placement to the spindle motor. In this manner, the overall size of the instrument 200 is made very compact and has a relatively small footprint. The spindle motor 242 can also be located on the opposite side of the baseplate 205.

FIG. 6 is a plan view of the double-crossover encoder spectrograph 200 shown in FIG. 4. As illustrated, radiation beams from two independent external sources 224-A and 224-B are imaged through corresponding samples 226-A and 226-B and onto corresponding entrance apertures 101-A and 101-B. The corresponding diffraction gratings 202-A and 202-B produce corresponding dispersed images at two different locations on the surface of the encoder disc 104 after passing through the respective encoder apertures 111-A and 111-B. As the encoder disc 104 rotates, the dispersed images thereon are simultaneously encoded to provide two independently encoded radiation beams, which are focused onto the detectors 209-A and 209-B. The signals produced by the detectors 209-A and 209-B are then provided to and analyzed by a computer to determine the spectral properties of each of the radiation sources 224-A and 224-B. In this manner, a single instrument 200 having a single encoder disc 104 (i.e., a single moving part) can be used to analyze two independent radiation sources 224-A and 224-B. In this way, a single encoder disc 104 and a single spindle motor 242 are used to analyze radiation transmitted through two different sources 224-A and 224-B or to analyze radiation transmitted through a common sample 226 and/or with different path lengths.

In an alternate embodiment, additional external optics are used to split radiation from a single source into two beams to provide input radiation for the encoders A and B. In this manner, a single instrument 200 having a single encoder disc 104 (i.e., a single moving part) can be used to analyze simultaneously a single radiation source 224 in two independent spectral ranges or to analyze simultaneously a single radiation source 224 altered by two distinct samples 226-A and 226-B.

Preferably, the diffraction gratings 202-A and 202-B, and the detectors 209-A and 209-B are selected and/or optimized for the analysis of their corresponding radiation sources 224-A and 224-B (or samples 226-A and 226-B). For example, the radiation sources 224-A and 224-B (or samples 226-A and 226-B) may have corresponding spectral features in different wavelength ranges that require different grating periods and/or detector types for detection and analysis. In such a case, different diffraction gratings 202-A and 202-B would be used where each grating 202-A and 202-B is tailored for the source 224-A and 224-B that is to be encoded.

In FIG. 6, radiation provided by the source 224-A and transmitted through the sample cell 226-A (e.g., a first liquid cell, gas cell, or ATR) is imaged on the corresponding entrance aperture 101-A, and radiation provided by the source 224-B and transmitted through the sample cell 226-B (e.g., a second liquid cell, gas cell, or ATR) is imaged on the corresponding entrance aperture 101-B. In this manner, a single instrument having a single encoder disc can be used to analyze two independent samples 226-A and 226-B.

If the sample is a gas, vapor or liquid, it may be advantageous to provide samples contained that have substantially identical constituents in substantially identical concentrations to facilitate the analysis of radiation transmitted through a common sample using different optical path lengths. For example by connecting the samples 226-A and 226-B with pneumatic tubing a continuous flowing sample (e.g., natural gas) can be simultaneously analyzed (compensating for flow latency, if required) using a short path cell to quantify the stronger absorbing (e.g., higher concentration) constituents and a long path cell to quantify the weaker absorbing (e.g., lower concentration) constituents. In this manner, the chemical concentration dynamic range is enhanced relative to instruments using a single sample cell with a fixed length.

Preferably, the radiation sources 224-A and 224-B, the sample cells 226-A and 226-B, the diffraction gratings 102-A and 102-B, and the detectors 209-A and 209-B, are selected and/or optimized for the analysis of the corresponding samples 226-A and 226-B, respectively. In FIG. 6, for example, the sample 226-A is depicted as providing a much shorter path length than the sample 226-B. The different sample size may be useful in situations where samples have constituents in wide-ranging concentrations (e.g., natural gas may have 85% methane and <1% hexane) or where samples of mixed phases (e.g., solid, liquids and gasses) are being analyzed. The illustration of transmission cells in FIG. 6 was chosen for clarity. Other sampling interfaces may be employed that utilize transmitted, reflected, scattered, or emitted radiation from samples in solid, liquid, gas, and/or vapor phases.

Temperature Compensation by Selecting Sign of Auto-Collimation Angle

The radius of encoder disc 104 and the nominal grating period of diffraction grating 102 increases with increasing temperature. As a consequence, the diffraction angle (as measured from the non-diffracted radiation beam) of a given wavelength component decreases with increasing temperature. It is advantageous to select the sign of the auto-collimation angle (i.e., diffraction order) such that zeroth order (non-diffracted) radiation is directed away from the center of the encoder disc. As temperature increases, the period of the diffraction grating 102 is reduced due to the expansion of the substrate material. This, in turn, moves the diffracted spectral components along the negative Y-axis (of FIG. 2) toward the zeroth-order or non-diffracted radiation beam. As temperature is increased, the radius of the encoder disc 104 increases due to the expansion of the substrate material, which moves the encoding tracks away from the axis of rotation (i.e., the center of the encoder disc 104).

To compensate for these temperature effects, in one embodiment, the sign of the auto-collimation angle is selected so that the two temperature effects compete against each another and, preferably, cancel each other out. Preferably, the sign of the auto-collimation angle of the diffraction grating 102 is selected so that the zeroth-order (i.e., non-diffracted) radiation is directed away from the disc center (i.e., axis of rotation). In this configuration, the change in the center wavelength of a given encoded component as a function of temperature is minimized.

Applications

A dual-spectrograph system operating in the Near Infrared (NIR) (e.g., using InGaAs, InAs, PbS, PbSe, thermopile or pyroelectric detectors) and Mid Infrared (MIR) (e.g., using PbSe, InSb, HgCdTe, thermopile or pyroelectric detectors) enables the consumer to compare in real-time chemometric analyses in two distinct spectral ranges, or to augment one with the other for improved reliability, dynamic range and/or accuracy. The dual-spectrograph system may be implemented using the dual encoder spectrograph architecture described herein. Other embodiments using other combinations of spectral ranges (e.g., ultra-violet (UV)-NIR and UV-MIR) may be used.

In another embodiment, a single instrument uses two spectrographs operating in different and distinct spectral regions (e.g., NIR and MIR), preferably mounted onto a single encoder. A sampling interface with two sampling sub-systems optimized for liquid (and/or solid) and gas (and/or vapor) phase samples. Each sampling sub-system is interfaced with one of the spectrographs to enable the simultaneous analysis of samples having both liquid and solid, liquid and gas (or vapor), and/or solid and gas constituents (i.e., mixed phase systems). Preferably, the sampling sub-systems (e.g., path length, temperature, and the like) and the corresponding spectrographs (e.g., spectral region, resolution, selection of encoded components, spectrum acquisition rate, and the like) are optimized for the analysis of the mixed-phase systems. For example, in a Liquid+Vapor Analyzer, the path length for the liquid sampling sub-system may be shorter that the path length for the vapor sampling sub-system, and/or the NIR spectral region may be used for the liquid analysis, and the MIR spectral region may be used for the vapor analysis. Such an instrument can be used for analyzing both the liquid and the headspace (i.e., the area above the liquid containing gasses or vapors) in fermentation vats, drums, solvent dryers, and other mixed-phase systems. This application can be implemented with a dual-spectrograph system as described herein.

In another embodiment, a single instrument uses two spectrographs interfaced with two sampling sub-systems: (1) an Attenuated Total Reflectance (ATR) system for analyzing solids (e.g., powders) and/or liquids; and (2) a gas cell for analyzing ambient air. In this manner, a first responder system can analyze samples at the scene of an incident while simultaneously monitoring the ambient environment for potential hazards (e.g., toxic and explosion hazards), all within a single instrument. This application can be implemented with a dual-spectrograph system as described herein.

Spectral-Library Interface for EPIR Analyzer

One challenge in the deployment of a new type of spectral instrument is the ability to share spectral information and compare results between two or more instruments. Because of manufacturing tolerances, the spectra produced by two encoder spectrographs are generally not expected to be identical. As such, algorithms are used to translate spectra for comparison purposes. Instrument specific spectral parameters (ISSPs) are the parameters that are used by such algorithms to enable spectra to be translated back and forth between two or more instruments.

Standard high-resolution (e.g., FTIR) reference spectra may be translated (e.g., masked and deresolved) using a model for the encoder-spectrograph's instrument specific spectral parameters (ISSPs) (e.g., dispersion function and radiation filter configuration) to provide instrument-specific reference spectra (ISRS) that are fit to "as-measured" spectra to determine the ISSPs for the encoder spectrograph. The spectral parameters enable the precise specification of the center wavelength and bandwidth for each encoded spectral component.

Reference spectra obtained from a spectral library may be processed (e.g., convolved) with the instrument's unique spectral parameters to provide instrument-specific reference spectra (ISRS). These ISRS are used with (e.g., compared to) "as-measured" spectra for chemometric analyses, e.g., a spectral library search to determine the origin of an unknown spectrum.

Existing calibrations can be transferred to the present invention by transforming high-resolution (e.g., FTIR) calibration spectra into instrument-specific calibration spectra (ISCS). The ISCS are then processed in the same manner as the original calibration spectra to generate an instrument-specific calibration (ISC). This process can be repeated on a number of instruments using their respective ISSPs to provide unique ISCS. In this manner, an existing calibration can be transferred onto one or more instruments.

In one embodiment, an algorithm that is compatible with the MyInstrument interface protocol, or other common data transfer or exchange format, inputs ISSPs and reference spectra from a spectral library and outputs provide instrument-specific reference spectra (ISRS) for use in the spectral analysis of an unknown sample.

In-Situ Phase Analysis for EPIR Analyzer Employing Orthogonal Encoded Components Having Substantially Identical Modulation Frequencies U.S. patent application Ser. No. 10/384,374 describes a modulator that provides pairs of encoded components having the same modulation frequency that are substantially orthogonal to one another. Since the maximum number of encoded unique harmonic components (i.e., each component encoded with a different harmonic of the fundamental rotation frequency of the modulator 104) is limited by the dispersed image width and the circumference of the outermost encoding track on the modulator, this approach enables the multiplexing of up to twice as many encoded components. One approach described in U.S. patent application Ser. No. 10/384,374 uses pairs of sinusoidal modulations that have the same frequency, but are 90 degrees out of phase (i.e., sines and cosines). The orthogonality of sine and cosine components having the same modulation frequency is limited by the uncertainty of the phase. It is therefore desirable to minimize the phase error to maximize inter-channel orthogonality.

In one embodiment, to minimize phase error and maximize orthogonality, an in-situ phase analysis based on prime-number encoded components is used. In a first step, two or more phase calibration components (PCCs) are provided with sine-only or cosine-only modulations. These PCCs are preferably prime-number harmonics of the fundamental rotational frequency, which are expected to have the least interference or cross-talk. The PCCs are then analyzed (e.g., using quadrature) to determine the phase of the encoded signals. A fit is generated between the resulting PCC phase and the modulation frequency and/or modulator radius using an appropriate model (e.g., a polynomial in modulation frequency and/or modulator radius). The resulting phase verses modulation frequency and/or modulator radius model is then applied to the other encoded components to maximize the orthogonality of sine and cosine components having the same modulation frequency.

TABLE 1

| Harmonic | Phase | $R_0$ | $\Delta R$ | PCC |
|---|---|---|---|---|
| 23 | 0 | 33.6932 | 0.0404 | yes |
| 24 | 0 | 33.774 | 0.0404 | no |
| 24 | 90 | 33.8549 | 0.0404 | no |
| 25 | 90 | 33.9358 | 0.0404 | no |
| 25 | 90 | 34.0166 | 0.0404 | no |
| 26 | 0 | 34.0974 | 0.0404 | no |
| 26 | 90 | 34.1782 | 0.0404 | no |
| 27 | 0 | 34.259 | 0.0403 | no |
| 27 | 90 | 34.3398 | 0.0403 | no |
| 28 | 0 | 34.4205 | 0.0403 | no |

TABLE 1-continued

| Harmonic | Phase | $R_0$ | $\Delta R$ | PCC |
| --- | --- | --- | --- | --- |
| 28 | 90 | 34.5013 | 0.0403 | no |
| 29 | 0 | 34.582 | 0.0403 | yes |

Table 1 describes a portion of an embodiment of the encoder disc 104 that uses 144 different harmonics to encode 256 different spectral components, to illustrate an embodiment of the invention where 32 prime number PCCs are used to provide input for the phase calibration algorithm. The table illustrates a case in which seven different harmonics are used to encode twelve different spectral components at twelve different radii on the surface of encoder disc 104. The table entries correspond to the (sinusoidal) radiation filter harmonic, the patterned phase, radial position ($R_0$), radial width ($\Delta R$), and whether the encoded component is a PCC. As shown in the table, the encoded components that are not designated as PCCs are used in pairs having the same modulation frequency (i.e., harmonic of the rotation frequency of encoder disc 104), which are modulated at 0 and 90 degrees, respectively. In contrast, the PCCs are not paired and are all modulated at a phase of 0 degrees. To assign the correct proportion of the amplitude to the two encoded components comprising the pair of components having the same modulation frequency (i.e., the non-PCCs), the phase of the signal as measured by the detector 209 at the modulation frequency of the pair must be known.

The phase as measured by the detector 209 (signal phase) is different from the patterned phase of the encoder disc 104 due to the frequency response of the detector electronics and because of non-lineal aberrations of the dispersed image along the radial axis of encoder 104. In one embodiment, to mitigate these uncertainties in the signal phase and recover the correct proportion of the amplitude to the two encoded components comprising the pair of components having the same modulation frequency, the phases of the PCCs are determined and an interpolation is used between the PCCs to estimate the signal phase of the non-PCC components.

In Table 1, for example, the signal phase of the 23rd harmonic and the 29th are determined by taking the arctangent of the sine and cosine projections of these harmonics relative to a global reference phase (e.g., as defined by an analysis of one or more of the signals provided by the rotary encoder 244 or a persistent feature in the detector signal, such as a centerburst). Once the signal phase of the 23rd and 29th harmonics have been determined, the signal phase of the components of the 24th through the 28th harmonics that have the same patterned phase as the PCCs (i.e., 0 degrees in Table 1) can be estimated by interpolation (e.g., using the radial position and/or the modulation harmonic as the abscissa). The corresponding signal phases for the 24th through the 28th harmonic components that have patterned phase different from the PCCs (i.e., 90 degrees in Table 1) are determined by interpolation and adding or subtracting the phase difference between the component and the PCC (e.g., 90 degrees). Once the signal phases of the 24th through the 28th harmonic components have been estimated, the proper proportion of the amplitudes at a given harmonic can be assigned to the two out-of-phase components using the corresponding trigonometric projections.

In another embodiment, the phase calibration described above is performed as a background task, at periodic intervals, or in response to external triggers (e.g., a change in the temperature as measured by temperature sensor 213). Preferably, the phase calibration algorithm uses the PCC signal amplitudes to weight the importance of the PCCs in the fitting routine. In this manner, a poor fit resulting from a strong absorbance in one or more of the PCCs can be prevented.

Spectrometer Calibration Training Mode Employing Unique Spectra Sorting Algorithm One challenge in developing a new chemometric application to identify and quantify analytes by analyzing unknown spectra is acquiring the proper reference spectra required for the underlying calibration. The calibration training spectra are the set of spectra required to build a calibration (e.g., construct a complete set of variance spectra) for a given chemometric application. There are many recommendations in the literature for selecting the calibration training spectra, but from a mathematical perspective, the requirement is simply to include all anticipated unique spectra—i.e., spectra that are not simply related to one another by an amplitude scale factor in the absorbance regime (or equivalently, a power factor in the transmission regime) or are simply linear combinations of two or more calibration training spectra.

An embodiment of the invention enables user to collect the calibration training spectra without having to follow a complicated script. The embodiment analyzes a continuous stream of spectra acquired during a calibration training mode and automatically logs those unique spectra required to build chemometric calibration model (hereafter referred to as "calibration training spectra"). A unique spectra sorting algorithm (USSA) determines if a new spectrum is unique within the growing set of calibration training spectra by comparing the new spectrum to each of the existing calibration training spectra (e.g., by fitting the new spectrum to each of the calibration training spectra using an amplitude scaling parameter in the absorbance regime or a power scaling parameter in the transmission regime). The algorithm then calculates a residual spectrum by subtracting the scaled new spectrum from the existing calibration training spectrum. A residual score is calculated for the new spectrum for each of the existing calibration training spectra (e.g., by comparing the integrated absorbance of the residual spectrum to a user-defined threshold). The residual scores are sorted to identify the minimum residual score, which identifies the calibration training spectrum that is the closest match to the new spectrum.

If the minimum residual score is determined to be significant, the new spectrum is deemed to be unique and is added to the set of calibration training spectra. If the spectra is determined not to be unique but corresponds to a higher amplitude (or concentration) version of an existing spectrum (e.g., the absorbance amplitude scaling parameter is greater than 1), the new spectrum overwrites the existing unique spectrum. In this manner, spectra with the highest signal-to-noise ratio are retained in the set of unique calibration training spectra.

The term spectrum as used herein has a broad definition, and the term includes selected portions of the entire spectrum measured by the instrument. In this manner, spectra from non-overlapping analytes can be separated from one another in mixtures to prevent unnecessary growth in the number of calibration training spectra.

In one embodiment, a graphical user interface (GUI) enables the user to "tag" spectra with analyte species and concentration information. Preferably, the GUI allows the user to tag spectra during the collection of the calibration training spectra and presents the user with a summary graph of the amplitude of the unique spectra versus time at the conclusion of the training session. This allows the user to verify and correct existing tags or add additional tags to the training set. In another embodiment, responsive to a user click on the graph the GUI presents a graph of one or more selected unique calibration training spectra, which can then be compared with spectra from a spectral library or other database for further verification of assigned tags.

In another embodiment, the calibration training spectra are stored in a database within the instrument that produced them, and the internal database are synchronized with or otherwise transferred to an external database (e.g., via the Internet) to enable access to the calibration training spectra for the development of chemometric calibrations. Preferably, the externally developed chemometric calibration is then transferred into the instrument's internal database for an appropriate chemometric application.

SUMMARY

While the invention has been described above by reference to various embodiments, it will be understood that different combinations, changes and modifications may be made without departing from the scope of the invention, which is to be defined only by the appended claims and their equivalents.

For example, instead of using the specific optical elements in the specific order as described, including the placement of a sample cell, or sample collection in the beam path, other optical elements, optical systems, or arrangements may be used without departing from the scope of the invention. Moreover, a transmissive spatial light modulator can also be used with the encoder spectrograph with appropriate changes to the configuration of the optical elements. One embodiment of the encoder spectrograph can encode radiation in the 3 to 5-micron spectral range; however, persons of ordinary skill in the art will understand that with minor modifications (e.g., grating line spacing, holographic etching pattern, auto-collimation angle, detector lens material/coating, and/or detector type) the encoder spectrograph can be embodied to encode radiation in other spectral regions.

These and other variations are within the scope of the invention. Accordingly, the foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above teachings. It is therefore intended that the scope of the invention be limited not by this detailed description, but rather by the claims appended hereto.

What is claimed is:

1. An encoder spectrograph for encoding and detecting one or more spectral components of a radiation beam, the encoder spectrograph comprising:
   a concave diffraction grating that disperses a received incident beam of radiation by wavelength;
   a crossover focusing reflector that redirects the dispersed beam across the incident beam to form an image dispersed by wavelength along a dispersion axis;
   a spatial light modulator positioned to receive the dispersed image on a surface thereof, the spatial light modulator modulating the intensity of the dispersed image by a position along the dispersion axis to provide an encoded beam;
   a crossover fast collection optic that collects the encoded beam from the spatial light modulator and redirects the encoded beam across the dispersed beam;
   a detector lens that focuses the encoded beam to form a substantially overlapping image; and
   a detector element positioned to receive the overlapping image and produce a signal representative of the encoded beam.

2. The encoder spectrograph of claim 1, wherein the concave diffraction grating, the crossover focusing reflector, the crossover fast collection optic, and the detector lens each have an optical center that is located in a substantially common plane.

3. The encoder spectrograph of claim 2, wherein the common plane is parallel to a perpendicular bisector of a midpoint of the dispersed image.

4. The encoder spectrograph of claim 1, wherein the concave diffraction grating, the crossover focusing reflector, the crossover fast collection optic, and the detector lens each have a vertex that is located in a substantially common plane.

5. The encoder spectrograph of claim 1, wherein the concave diffraction grating is mounted at an inclination angle so that the crossover focusing reflector just clears the incident beam.

6. The encoder spectrograph of claim 1, wherein the spatial light modulator reflects the dispersed image towards the crossover fast collection optic.

7. The encoder spectrograph of claim 1, wherein the received incident beam is substantially parallel to a detector axis normal to the detector element.

8. The encoder spectrograph of claim 1, wherein the received incident beam and a detector axis normal to the detector element are substantially parallel to the surface of the spatial light modulator.

9. The encoder spectrograph of claim 1, wherein the diffraction grating is mounted at an inclined auto-collimation angle so that the diffraction angles of the diffraction grating are symmetric about a midpoint of the dispersed beam.

10. The encoder spectrograph of claim 1, wherein the spatial light modulator comprises a rotating disc having a plurality of radiation filters located at different radii from a rotation axis, the radiation filters corresponding to positions along the dispersion axis.

11. The encoder spectrograph of claim 10, further comprising:
    a motor for rotating the spatial light modulator about the rotation axis, the motor, the concave diffraction grating, the crossover focusing reflector, the crossover fast collection optic, and the detector lens located on the same side of the spatial light modulator.

12. The encoder spectrograph of claim 10, wherein the concave diffraction grating and the detector element are located on opposite sides of the rotation axis of the spatial light modulator.

13. The encoder spectrograph of claim 1, wherein the spatial light modulator comprises an addressable LCD.

14. The encoder spectrograph of claim 1, wherein the spatial light modulator comprises a MEMS device.

15. The encoder spectrograph of claim 1, wherein a portion of the detector lens is cut away to prevent mechanical interference with the incident beam.

16. The encoder spectrograph of claim 1, wherein a portion of the crossover fast collection optic is cut away to prevent mechanical interference with the dispersed beam.

17. The encoder spectrograph of claim 1, further comprising:
an entrance aperture, the received incident beam passing through the entrance aperture towards the concave diffraction grating.

18. The encoder spectrograph of claim 1, further comprising:
a detector aperture, the overlapping image passing through the detector aperture from the detector lens towards the detector element.

19. The encoder spectrograph of claim 1, the spatial light modulator having a circular shape and a diameter in a plane containing the surface of the modulator, wherein an optical path from the spatial light modulator to the detector element is less than the diameter of the spatial light modulator.

20. The encoder spectrograph of claim 19, wherein the overlapping image on the detector element is less than 4 mm in any dimension.

21. The encoder spectrograph of claim 1, wherein the crossover fast collection optic and the detector lens are the only optical elements in an optical path between the spatial light modulator and the detector element.

22. The encoder spectrograph of claim 1, further comprising:
a printed circuit board coupled to the detector element for receiving signals representing the overlapping image, the printed circuit board having a cutaway portion through which the received incident beam passes.

23. The encoder spectrograph of claim 1, wherein the crossover focusing reflector, the crossover fast collection optic, and the detector lens are mounted in a single optics bracket.

24. The encoder spectrograph of claim 23, wherein the concave diffraction grating is mounted in a grating mount that is detachably attachable to the optics bracket.

25. The encoder spectrograph of claim 1, wherein the crossover focusing reflector, the crossover fast collection optic, and the detector lens are combined into a single injection-molded optics bracket.

26. The method of claim 25, wherein the crossover focusing reflector and the crossover fast collection optic are formed by evaporating metallic surfaces on the injection-molded optic.

27. An encoder spectrograph for encoding and detecting one or more spectral components of a received radiation beam, the encoder spectrograph comprising:
first optics dispersing a received incident beam of radiation by wavelength and redirecting the dispersed beam across the incident beam to form an image dispersed by wavelength along a dispersion axis;
a spatial light modulator positioned to receive the dispersed image on a surface thereof, the spatial light modulator modulating the intensity of the dispersed image by a position along the dispersion axis to provide an encoded beam;
second optics collecting the encoded beam from the spatial light modulator, redirecting the encoded beam across the dispersed beam, and focusing the encoded beam to form a substantially overlapping image; and
a detector element positioned to receive the overlapping image and produce a signal representative of the encoded beam.

28. The encoder spectrograph of claim 27, wherein the second optics consists solely of a single reflective element and a single lens element.

29. A dual encoder spectrograph for encoding and detecting one or more spectral components of each of two received radiation beams, the encoder spectrograph comprising:
first dispersing optics dispersing a first received incident beam of radiation by wavelength and redirecting the first dispersed beam across the first incident beam to form a first image dispersed by wavelength along a first dispersion axis;
second dispersing optics dispersing a second received incident beam of radiation by wavelength and redirecting the second dispersed beam across the second incident beam to form a second image dispersed by wavelength along a second dispersion axis;
a spatial light modulator positioned to receive the first and second dispersed images on a surface thereof, the spatial light modulator modulating the intensity of each of the first and second dispersed images by a position along the corresponding first and second dispersion axes to provide a first encoded beam and a second encoded beam;
first collecting optics collecting the first encoded beam from the spatial light modulator, redirecting the first encoded beam across the first dispersed beam, and focusing the first encoded beam to form a substantially first overlapping image; and
second collecting optics collecting the second encoded beam from the spatial light modulator, redirecting the second encoded beam across the second dispersed beam, and focusing the second encoded beam to form a substantially overlapping second image;
a first detector element positioned to receive the first overlapping image and produce a first signal representative of the first encoded beam; and
a second detector element positioned to receive the second overlapping image and produce a second signal representative of the second encoded beam.

30. The encoder spectrograph of claim 29, wherein the first and second incident beams are received on the same side of the dual encoder spectrograph.

* * * * *